United States Patent
Momiuchi et al.

(10) Patent No.: US 7,082,151 B2
(45) Date of Patent: Jul. 25, 2006

(54) LASER DEVICE AND OPTHALMOLOGICAL SURGICAL SYSTEM

(75) Inventors: Masayuki Momiuchi, Tokyo-to (JP); Taizo Eno, Tokyo-to (JP); Yoshiaki Goto, Tokyo-to (JP); Hideo Sagehashi, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 120 days.

(21) Appl. No.: 10/675,015

(22) Filed: Sep. 30, 2003

(65) Prior Publication Data

US 2004/0078029 A1    Apr. 22, 2004

(30) Foreign Application Priority Data

Oct. 18, 2002    (JP)    ............................. 2002-304955

(51) Int. Cl.
*H01S 3/08* (2006.01)
(52) U.S. Cl. ............................. 372/99; 372/92; 372/98
(58) Field of Classification Search ................ 372/22, 372/21, 34, 99, 98
See application file for complete search history.

(56) References Cited

U.S. PATENT DOCUMENTS

| 5,171,242 A | 12/1992 | Dewey et al. ................. 606/4 |
| 6,711,184 B1* | 3/2004 | Hollemann et al. ........... 372/22 |
| 2003/0195495 A1* | 10/2003 | Ryan et al. .................... 606/15 |

FOREIGN PATENT DOCUMENTS

JP    8-196561    8/1996

OTHER PUBLICATIONS

CLEO 2001 Short Course Notes—3 pages.

* cited by examiner

*Primary Examiner*—Minsun Oh Harvey
*Assistant Examiner*—Dung Nguyen
(74) *Attorney, Agent, or Firm*—Nields & Lemack

(57) ABSTRACT

A laser device, comprising a laser beam emitter having an optical resonator, wherein the optical resonator has a resonator and a reflection mirror, and at least one of a length of the resonator or a curvature of the reflection mirror is determined so as to satisfy condition that a parameter $M^2$ of beam quality of a projected laser beam is within a range of $8 \leq M^2 \leq 22$, where $M^2 = \pi W \cdot \Theta / \lambda$ (W is a beam waist of a laser beam; $\Theta$ is a spreading angle; and $\lambda$ is a wavelength of the laser beam).

4 Claims, 4 Drawing Sheets

LASER DEVICE AND OPTHALMOLOGICAL SURGICAL SYSTEM

BACKGROUND OF THE INVENTION

The present invention relates to a laser device, in particular, a laser device used in an ophthalmological surgical system such as a photocoagulator. Also, the invention relates to an ophthalmological surgical system equipped with the laser device.

In recent years, a type of ophthalmological surgical system has been propagated, by which it is possible to perform photocoagulation, resection, incision, etc. of a site to be treated on non-contact basis by using high energy density of a laser beam and operation can be performed by preventing hemorrhage and without risk of contamination with bacteria.

In the ophthalmological surgical system using a laser beam, a laser beam is projected to a site to be treated through a pupil of a human eye, and the procedures such as photocoagulation, resection, incision, etc. can be carried out.

FIG. 4 is a schematical drawing of a photocoagulator. In the figure, reference numeral 1 denotes a laser device, 2 is a condenser lens, 3 is an optical fiber for guiding a laser beam to a target position, 4 is a condenser lens, 5 is a human eye, and 6 represents a pupil of an eye.

A laser beam 10 with an opening angle θ emitted from the laser device 1 is converged by the condenser lens 2 and enters the optical fiber 3. The opening angle θ can be approximated to numerical aperture NA. In the following, description will be given by referring the opening angle as numerical aperture NA. The laser beam 10 enters the optical fiber 3 with numerical aperture NAi. The laser beam 10 is emitted from the optical fiber 3 with numerical aperture NAe. Further, the laser beam 10 is converged by the condenser lens 4 and is projected to the human eye 5. Among the light components of the laser beam 10 converged by the condenser lens 4, the light components corresponding to numerical aperture NAm of the pupil 6 are projected to an eye fundus of the human eye 5, and photocoagulation is performed on an affected site.

FIG. 5 shows relation of numerical aperture NAi of the laser beam 10 entering the optical fiber 3, numerical aperture NAe of the laser beam 10 emitted from the optical fiber, and numerical aperture NAf of the optical fiber 3. These numerical apertures have a relation of: NAi<NAe<NAf.

In the photocoagulator as described above, if the laser beam 10 emitted from the optical fiber 3 is directly projected to the human eye 5, the numerical aperture of the pupil 6 is: NAm≦0.06. The numerical aperture of the optical fiber 3, from which the laser beam 10 is emitted, is: NAf=0.12. Therefore, when the numerical aperture of the laser beam 10 entering the optical fiber 3 is big, the numerical aperture of the laser beam 10 emitted from the optical fiber 3 is also increased more compared with the numerical aperture NAm of the pupil 6.

When the laser beam 10 emitted from the optical fiber 3 projects an optical fiber image to a retina in equal size or in reduced size and photocoagulation is performed, peripheral portion of the laser beam 10 is interrupted by the pupil 6 as shown in FIG. 4. Only the luminous flux near the center of the laser beam 10 can be projected to the eye fundus, and optical loss is extremely increased. No trouble occurs if the laser beam 10 emitted from the laser device 1 has sufficient light amount. However, in case a semiconductor laser is used as a light source of the laser device 1, it is difficult to have higher light amount of the laser beam 10 to reach the eye fundus, and it is not easy to have the light amount sufficient for the treatment.

If the numerical aperture NAi of the laser beam 10 entering the optical fiber 3 is decreased, the numerical aperture NAe of the exit laser beam 10 is also decreased, and the loss of the laser beam projected to the eye fundus through the pupil 6 can be decreased. Therefore, it is generally practiced to project the laser beam to the optical fiber 3 by decreasing the numerical aperture NAi of the laser beam 10 emitted from the laser device 1.

However, when the numerical aperture of the laser beam 10 to enter the optical fiber 3 is decreased, light intensity distribution at a projected point is made uneven due to interference between propagation modes excited when the laser beam 10 passes through the optical fiber 3. FIG. 6(C) and FIG. 6(D) show the conditions of the laser beam 10 at the projected point in condition that interference occurs. FIG. 6(A) and FIG. 6(B) show the light intensity of the laser beam 10 is uniform, and light intensity distribution is in form of a top hat. When these two cases are compared with each other, speckled spots are seen at the projected point in case of the laser beam 10 with interference, and it is apparent that there is extreme variation in the light intensity distribution. When photocoagulation operation is performed, the speckled spots at the projected point and light intensity distribution of the laser beam 10 exert influence on the therapeutic effects.

For this reason, it has been practiced in such manner that the laser beam emitted from the optical fiber has uniform light intensity by using optical members such as a micro lens array, an axicon lens etc. This is described, for instance, in: CLEO 2001, Short Course Notes, SC117, Laser Beam Analysis, Propagation, and Shaping Techniques, written by James R. Leger, published on May 7, 2001.

A simple method is known, by which focus is not formed on a retina but it is turned to de-focused state, and non-uniformity of the light intensity is averaged. This is described, for instance, in JP-A-8-196561.

In the conventional method as described above, which uses optical members such as a micro lens array, an axicon lens, etc. to equalize the light intensity, many component parts are required and this leads to higher cost. In the method to turn to de-focused state and to equalize and average the non-uniformity of the light intensity, there has been problems such that it is difficult to maintain the de-focused state.

SUMMARY OF THE INVENTION

It is an object of the present invention to provide a laser device, which gives uniform light intensity distribution at a projected point and which can be used by simple procedure and gives lower optical loss.

To attain the above object, the laser device according to the present invention comprises a laser beam emitter having an optical resonator, wherein the optical resonator has a resonator and a reflection mirror, and at least one of a length of the resonator or a curvature of the reflection mirror is determined so as to satisfy condition that a parameter $M^2$ of beam quality of a projected laser beam is within a range of $8 \leq M^2 \leq 22$, where $M^2 = \pi W \cdot \Theta / \lambda$ (W is a beam waist of a laser beam; Θ is a spreading angle; and λ is a wavelength of the laser beam).

Also, the present invention provides an ophthalmological surgical system, comprising the laser device described above, wherein the laser device emits a laser beam in such manner that a parameter $M^2$ of beam quality is within a range of $8 \leq M^2 \leq 22$.

Furter, the present invention provides a laser device described above, wherein the laser beam emitted from the laser beam emitter is propagated in an optical fiber, wherein a core diameter of the optical fiber is from 50 μm to 75 μm, and numerical aperture NAf of said optical fiber is 0.10~0.12. Also, the present invention provides a laser device described above, wherein the laser beam emitted from the laser beam emitter is propagated in an optical fiber, wherein exit numerical aperture NAe of the laser beam emitted from the optical fiber is $0.06 \leq NAe \leq 0.1$.

BRIEF DESCRIPTION OF THE DRAWINGS

FIG. 6(A) and FIG. 6(B) each represents a case where the light intensity distribution of the laser beam is uniform, and FIG. 6(C) and FIG. 6(D) each shows a case where the light intensity distribution is not uniform.

DETAILED DESCRIPTION OF THE PREFERRED EMBODIMENT

Figure 1:
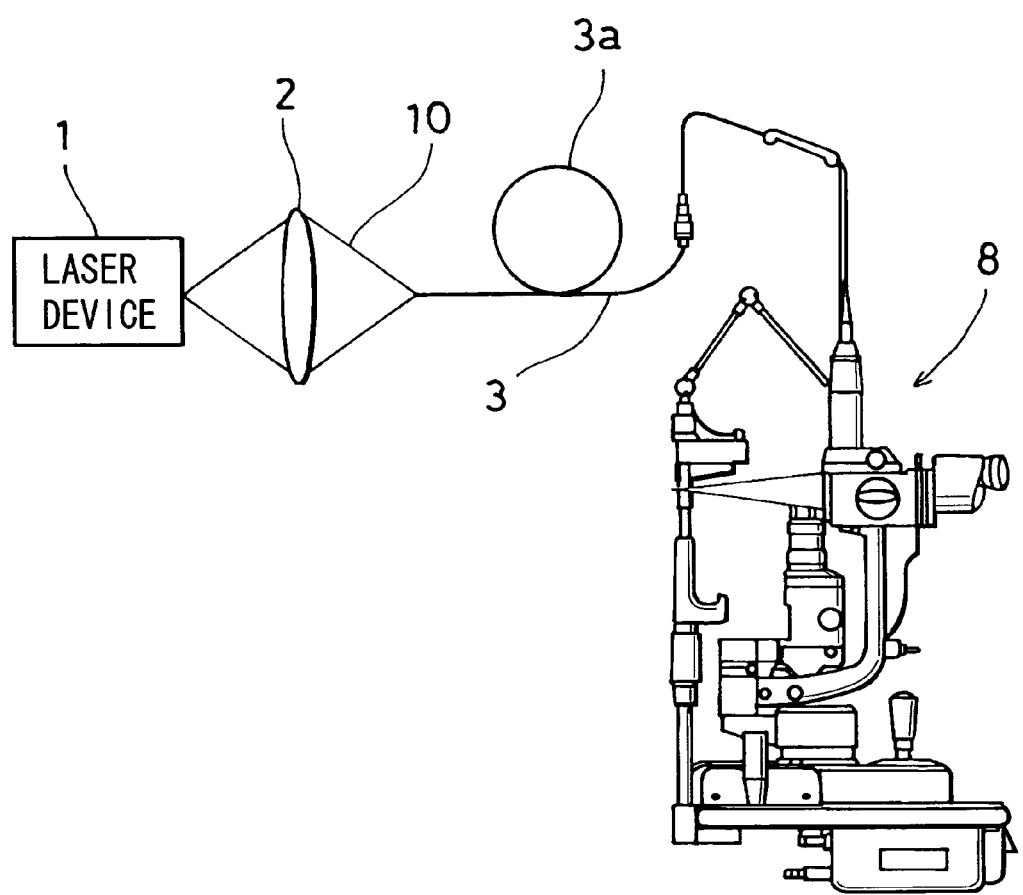
FIG. 1 is a drawing schematically illustrating an embodiment of the present invention.

Description will be given below on an embodiment of the present invention referring to the drawings.

Figure 4:
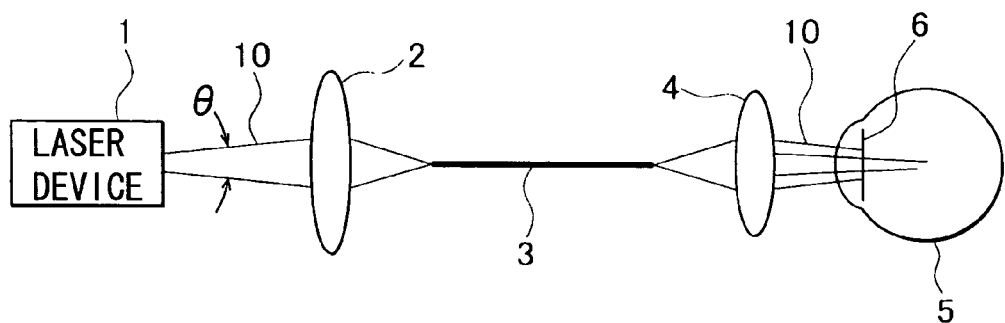
FIG. 4 is a schematical drawing of a conventional type photocoagulator.

FIG. 1 is a schematical drawing to illustrate a photocoagulator. In the figure, the same component as shown in FIG. 4 is referred by the same symbol. Reference numeral 1 denotes a laser device, 2 denotes a condenser lens, 3 is an optical fiber, and 8 represents a slit lamp. The optical fiber 3 comprises a loop unit 3a, which excites all of propagation modes of the laser beam 10, propagating within the optical fiber 3, prevents interference between the propagation modes and provides uniform light intensity distribution.

As described above, in order that the laser beam 10 emitted from the laser device 1 is propagated well when the laser beam 10 enters the optical fiber 3, and that the laser beam 10 is propagated with high efficiency from the optical fiber 3 to the slit lamp 8 and to human eyes (not shown), the laser beam must have a small opening angle θ and high beam quality. However, when the beam quality is too high, interference occurs between propagation modes excited within the optical fiber 3. As a result, strong intensity unevenness or speckle noise may develop in light intensity distribution of the irradiated light, and this hinders therapeutic effects.

On the other hand, to eliminate intensity unevenness and to have uniform distribution, a laser beam with lower quality is required, which can propagate in multiple modes, causing no mode competition. However, when beam quality is low, optical coupling with the slit lamp 8 is poor, and this leads to higher optical loss.

In the laser device according to the present invention, special notice is given on the fact that optical loss (transmission loss) during the coupling between optical members of an optical system and light intensity distribution at a projected point are all related with beam quality. Thus, according to the present invention, uniform light intensity distribution is maintained and the laser beam 10 are emitted with a beam quality, which can suppress transmission loss.

First, $M^2$ is a parameter to express the quality of the laser beam 10. $M^2$ is defined as follows:

$$W = M\omega$$

$$\Theta = M\theta$$

$$\theta = \lambda/(\pi\omega)$$

$$W \cdot \Theta = M^2(\omega \cdot \theta)$$

$$= M^2 \lambda/\pi$$

where W is a beam waist, and Θ is a spreading angle.

Here, the symbols ω and θ denote a beam waist and a spreading angle of a fundamental mode (Gauss beam) of the laser beam 10 with a wavelength λ respectively. The deviation of the laser beam 10 from the fundamental mode is expressed as $M^2$ (M). It is a preservable quantity under a lens optical system.

The same definition can be applied to the laser beam 10, which is propagated in the optical fiber 3. If it is assumed that D is a diameter of a converged beam to the optical fiber 3 (with core diameter of φ and numerical aperture of NAf), and that incident NAi is numerical aperture of the beam, the condition of coupling to the optical fiber 3 can be expressed by an equation given below by taking full consideration on the coupling condition (D ≤ φ, NAi ≤ NAf). In the equation, NAe represents exit NA of the laser beam 10 emitted from the optical fiber 3.

$$W \cdot \Theta = M^2 \lambda/\pi$$

$$= D \cdot NAi/2$$

$$\leq \phi \cdot NAe/2 (NAi \leq NAe \leq NAf)$$

As a result, the following equation can be obtained:

$$M^2 = (\pi\phi/2\lambda) \cdot NAe$$

In general, when the laser beam 10 enters the optical fiber 3 in a multiple mode, beam product (W·Θ) is not preserved, and it depends on the length of the optical fiber 3 and on a curvature of the loop unit 3a, and beam quality is deteriorated to a value (φ·NAf/2), which is determined by the characteristics of the fiber. However, when the length of the optical fiber 3 is several meters and the loop unit 3a has big curvature, deterioration is low, and the characteristics of the laser beam 10 when it enters the optical fiber 3 are substantially reflected. The lower limit of the incident NA to the optical fiber 3 can be judged from the uniformity of cross-sectional intensity distribution of the projected laser beam 10.

When the value of NA is decreased and the quality of the laser beam 10 is increased too much, the propagation mode within the optical fiber 3 is excited, and give-and-take (i.e. interference) of energy occurs between the propagation modes. As a result, strong intensity unevenness and speckle noise occur in the intensity distribution of the exit light. In surgical operation, this causes unevenness in coagulation and impairs the therapeutic effects. Even when the beam quality may be high and the beam can enter human eyes (not shown) at a value of NA smaller than NAm, the beam cannot be used for the operation if interference noise is high.

It is difficult to clearly define the light intensity distribution, while a cross-sectional light intensity distribution in form of a top hat and similar to refractive index distribution (step index) of the optical fiber 3 is considered to be optimal. Therefore, if deviation from the average value is defined as noise, it is required that the deviation Δ is within an allowable value. If it is assumed that light intensity distribution at an arbitrary point within the cross-section of the laser beam 10 is I (x, y), and that the average value within the cross-section is <I>, the deviation Δ can be defined by the following equations:

$$\Delta = \iint (I - <I>)^2 dx dy / <I>^2$$

$$<I> = \iint I(x, y) dx dy$$

Figure 5:
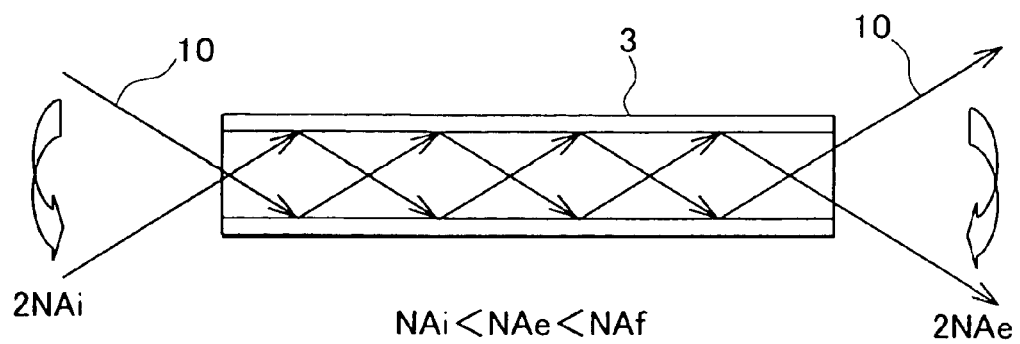
FIG. 5 is a drawing to show a relation between numerical aperture of a laser beam entering an optical fiber and numerical aperture of a laser beam emitted from the optical fiber.
Figure 6:
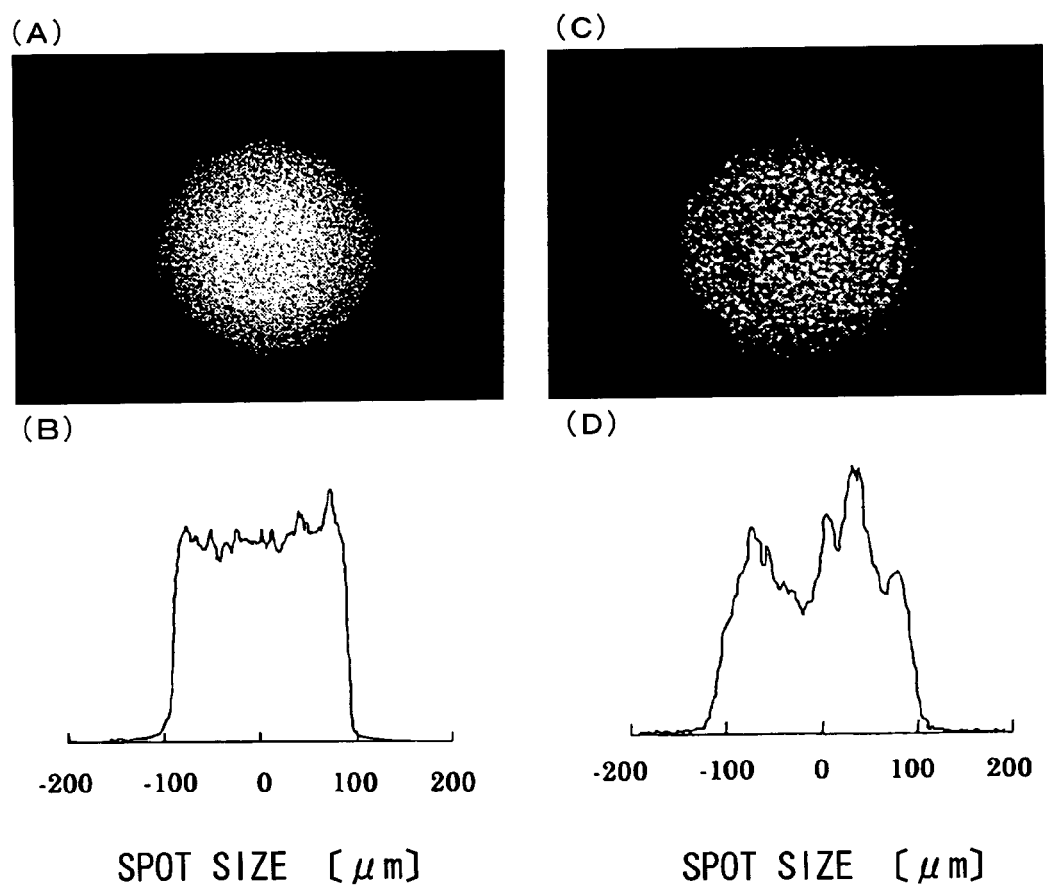
FIG. 6 represents illustrations and diagrams, each illustration showing speckled spots at an irradiation point of a laser beam and each diagram showing light intensity distribution respectively.

Empirically, the noise is decreased to less than Δmax, which is considered to be low noise when the incident NA to the optical fiber 3 is NAmin or more, NAmin≦NA≦NAe On the other hand, in an optical system of the slit lamp 8, beam product (W·Θ) can be preserved. When photocoagulation is carried out by projecting an optical fiber image to a retina in equal size or in reduced size, the characteristics of a therapeutic light from the slit lamp 8 is restricted by NAm of the pupil 6. Specifically, even when the light beam enters the slit lamp 8 with a spreading angle Θ, which is larger than NAm, the light does not contribute to the treatment, and only optical loss occurs. Thus, the maximum exit NAmax from the optical fiber 3, which is allowable in a photocoagulator, is between NAm and NAf (See FIG. 5).

NAm≦NAmax≦NAf

Therefore, the following condition is obtained as the exit NA from the optical fiber 3.

NAmin≦NAe≦NAmax

From this, the allowable beam quality parameter $M^2$ is given as:

$M^2$min≦$M^2$≦$M^2$max

Figure 2:
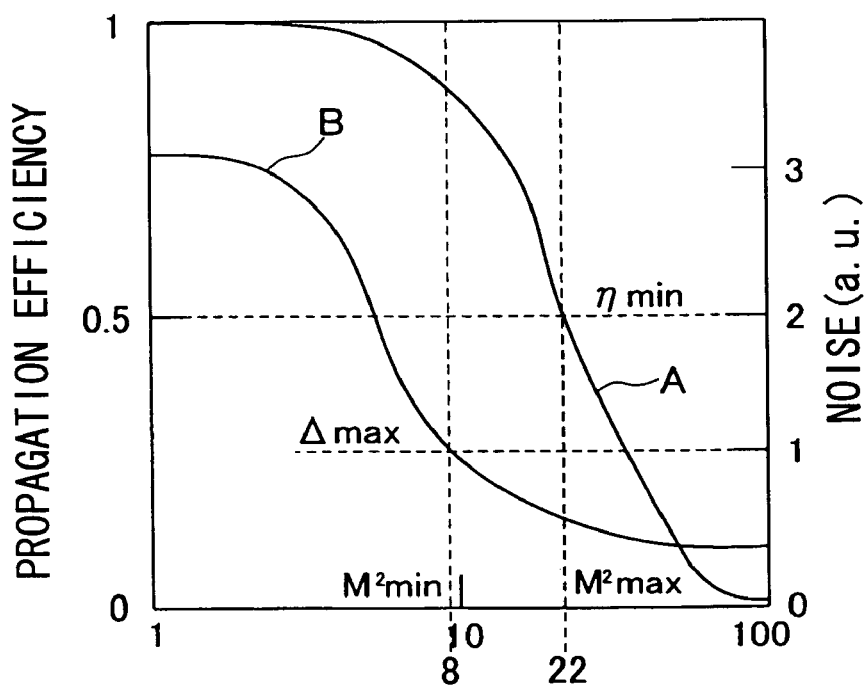
FIG. 2 is a diagram showing a typical relation between a propagation efficiency and $M^2$ and also a typical relation between noise and $M^2$.

FIG. 2 shows a typical relation between propagation efficiency and $M^2$ and a typical relation between noise and $M^2$. In the figure, the curve A represents propagation efficiency, and the curve B represents noise.

If it is assumed that propagation efficiency of the optical fiber 3 from the light source is 70% or more, and that propagation of the light from the optical fiber 3 to a cornea (eye fundus) is 70% or more, overall propagation efficiency of 50% or more can be expected.

ηmin≧50%   (1)

Also, if it is assumed that the allowable level of noise is within about ±10% of the average value, then:

Δmax≦1(a.u.)   (2)

The condition to satisfy the equations (1) and (2) at the same time is given from FIG. 2 as:

8≦$M^2$≦22

When the laser beam 10 is used, which has the beam quality parameter within this range, an optical fiber with a general core diameter of φ 50 μm (NAf=0.12) or an optical fiber with a general core diameter of φ 75 μm (NAf=0.12) can be used as the optical fiber for propagating the laser beam to the slit lamp 8. When the former optical fiber is used, from 8≦(πφ/2λ)·NAe≦22, overall propagation efficiency of 50% or more can be expected within the range of 0.06≦NAe≦NAf. It is preferable that NAf is 0.10~0.12.

When the latter optical fiber is used, overall propagation efficiency of 50% or more can be expected within the range of 0.06≦NAe≦0.1. Of course, cross-sectional light intensity distribution is uniform within this range. If the specification for the fiber is different, the exit allowable range of the optical fiber is also different, but the allowable range of beam characteristics of the laser beam is not changed. Further, allowable noise level must be correlated with the therapeutic effects. There is, however, no experimental record, and a typical value is obtained here.

Figure 3:
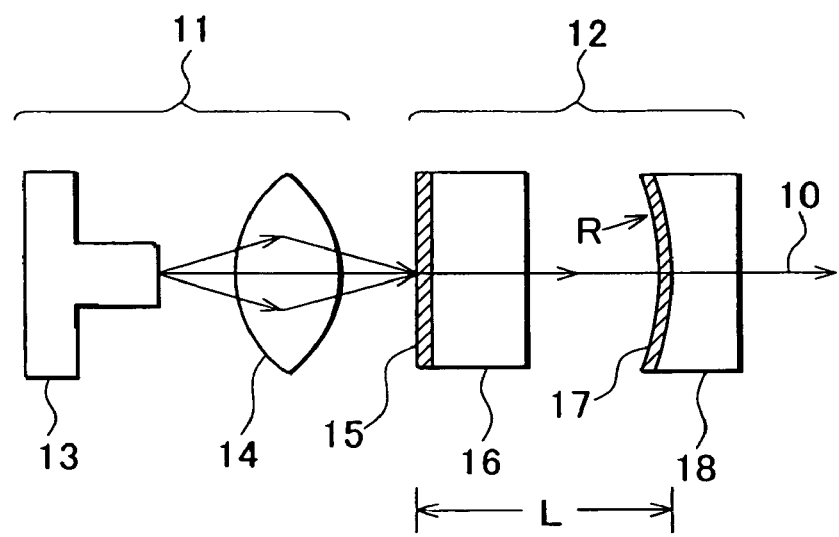
FIG. 3 is a drawing to explain an example of an LD solid-state excitation laser.

FIG. 3 shows an example of an LD solid-state excitation laser provided in the laser device 1. In FIG. 3, reference numeral 11 denotes a light emitter, and 12 denotes an optical resonator. The light emitter 11 comprises an LD light emitting source (semiconductor laser) 13 for emitting a laser beam 10 as excitation light, and a condenser lens 14. Further, the optical resonator 12 comprises a laser crystal (e.g. Nd:YVO$_4$) plate 16 where a dielectric reflection film 15 is formed and an output mirror 18 where a dielectric reflection film 17 is formed. At the optical resonator 12, the laser beam 10 is pumped, resonated, amplified and outputted.

The parameters giving strong influence to beam characteristics of the laser beam 10 are: length of a resonator (L), curvature of a mirror (R), overlapping of excitation volume and oscillation mode volume in an active medium, etc. For instance, beam waist ($\omega_0$) of the fundamental mode (TEM$_{00}$; $M^2$=1) in a plane-concave surface resonator can be given by the following equation:

$$\omega^2 = (\lambda/\pi)(L(R-L))^{1/2}$$

where the symbol λ represents oscillation wavelength.

In general, oscillation (lateral) mode is under influence of diffraction loss caused by Fresnel number as expressed by the equation given below. Oscillation begins from the oscillation mode of lower order.

$$N = a^2/(\lambda L)$$

In the above equation, "a" represents an aperture in the resonator. The higher the value of N is, the bigger the diffraction loss is, and the oscillation is inhibited. Normally, by increasing the value of L, the order of the oscillation mode is decreased, and oscillation is carried out in the fundamental mode. In contrast, if the value of L is at low level, oscillation occurs easily even in a multi-mode (TEM$_{mn}$; $M^2$>1). If excitation volume is bigger than the oscillation mode volume, oscillation occurs easily in the multi-mode. In general, oscillation is carried out in the fundamental mode. The radius $\omega_p$ of the excitation light is taken at a lower value than $\omega_0$ ($\omega_p<\omega_0$). In an excitation system using a high-output LD, it is set as ($\omega_p>\omega_0$). In this case, multi-mode oscillation volume other than the fundamental mode is also excited. Thus, oscillation takes place not only in the fundamental mode but also in high-order mode ($M^2$>1).

After all, when a shorter resonator is used and excitation is performed with excitation light with a radius larger than the beam waist of the fundamental mode, oscillation takes place in a plurality of multi-modes. In the embodiment given here, $M^2$ is ~10 under the condition that L~25 mm, R=100 mm, and $\omega_p$~0.4 mm. Naturally, the oscillation of lateral mode is also influenced by thermal lens effect of the laser medium and by a wavelength conversion crystal placed in the resonator. In this respect, it is difficult to fix $M^2$ to a certain fixed value, while it may not be difficult to control $M^2$ within a predetermined range.

According to the present invention, a laser device is provided, which comprises a laser beam emitter having an optical resonator, wherein the optical resonator has a resonator and a reflection mirror, and at least one of a length of the optical resonator or a curvature of the reflection mirror is determined so as to satisfy condition that a parameter $M^2$ of beam quality of a projected laser beam is within a range of $8 \leq M^2 \leq 22$. As a result, it is possible to suppress transmission loss and to obtain therapeutic light, which has uniform light intensity distribution of the laser exit light from a slit lamp and which has high therapeutic effect without using a specific type of optical system.

Also, when an ophthalmological surgical system, e.g. a photocoagulator, is provided with a laser with an optimal beam parameter, transmission loss can be suppressed and the restriction to the laser device can be reduced. Also, uniform light intensity can be obtained in simple manner. As a result, a complicated optical system is not required, and the structure of the system can be simplified.

Further, an uniform laser beam can be obtained, which makes the light intensity distribution to a form of a top hat, and this contributes to the increase of the therapeutic effect.

What is claimed is:

1. A laser device, comprising a laser beam emitter having an optical resonator and an optical fiber for guiding a laser beam from said laser beam emitter, wherein said optical resonator has a resonator and a reflection mirror, wherein numerical apertures NAi, NAe and Naf have a relation of: NAi<NAe<NAf, where the numerical aperture of the laser beam entering said optical fiber is NAi, the numerical aperture of the laser beam emitted from said optical fiber is NAe, the numerical aperture of said optical fiber is NAf, and at least one of a length of said resonator or a curvature of said reflection mirror is determined so as to satisfy the condition that a parameter $M^2$ of beam quality of a projected laser beam is within a range of $8 \leq M^2 \leq 22$, where $M^2 = \pi W \cdot / \theta$ (W is a beam waist of a laser beam; $\theta$ is a spreading angle; and $\lambda$ is a wavelength of the laser beam).

2. A laser device according to claim 1, further comprising a slit lamp optical system, wherein the laser beam from said optical fiber enters a pupil of an eye via said slit lamp optical system, wherein the numerical apertures Nam and NAmax have a relation of: NAm $\leq$ NAmax $\leq$ NAf, where the numerical aperture of the pupil is Nam and the maximum numerical aperture of the laser beam is NAmax, and a parameter $M^2$ of beam quality is within a range of $8 \leq M^2 \leq 22$.

3. A laser device according to claim 1, wherein the laser beam emitted from said laser beam emitter is propagated in said optical fiber, wherein a core diameter of said optical fiber is 50 μm, and the numerical aperture NAe of the laser beam emitted from said optical fiber is in a range of $0.06 \leq NAe \leq NAf$.

4. A laser device according to claim 1, wherein the laser beam emitted from said laser beam emitter is propagated in said optical fiber, wherein a core diameter of said optical fiber is 75 μm, and the numerical aperture NAe of the laser beam emitted from said optical fiber is in the range of $0.06 \leq NAe \leq 0.1$.

* * * * *